United States Patent [19]

Tsai

[11] Patent Number: 4,686,966

[45] Date of Patent: Aug. 18, 1987

[54] DISPOSABLE DUCKBILL SPECULUM

[76] Inventor: Joy Y. Tsai, No. 54, Lane 1, Been Street, Tung Shih, Taichung Hsien, Taiwan

[21] Appl. No.: 850,853

[22] Filed: Apr. 11, 1986

Related U.S. Application Data

[63] Continuation-in-part of Ser. No. 832,431, Feb. 24, 1986.

[51] Int. Cl.[4] ............................................. A61B 1/30
[52] U.S. Cl. ....................................................... 128/17
[58] Field of Search .................................. 128/17, 18, 3

[56] References Cited

U.S. PATENT DOCUMENTS

| | | | |
|---|---|---|---|
| 3,716,047 | 2/1973 | Moore et al. | 128/18 |
| 3,815,585 | 6/1974 | Fiore | 128/17 |
| 3,890,961 | 6/1975 | Moore et al. | 128/17 |

OTHER PUBLICATIONS

George Tiemann & Co.'s Surgical Instruments, p. 439, ©1889.

Primary Examiner—William H. Grieb
Attorney, Agent, or Firm—Poms, Smith, Lande & Rose

[57] ABSTRACT

This invention is a kind of disposable gynecologic apparatus, that is, a duckbill speculum, for examining the vagina. This duckbill speculum comprises a lower bill section, an upper bill section, a support column and a pair of adjustment pieces which contain a bolt, an adjustment nut and a height adjustment bolt. Both bill sections are respectively produced as one piece and each has a duckbill-like bill wherein the two bills, lower and upper, respectively nearly perpendicularly connect to a stationary and an adjustable handle. The upper bill section and the support column are secured by two bill fasteners around both ends and thereby both can rotate around the bill fasteners. The support column can move up and down along the stationary handle of the lower bill section. Therefore, the height adjustment bolt enables the speculum to be adjusted or stretched to a desired width. Another bolt is secured to the support column and thereby a fixed open angle of two bills can be maintained by adjusting the adjustment nut. Furthermore, as this duckbill speculum is made of relatively cheap material, plastics or fiber-reinforced plastics, it can therefore be classified as a disposable apparatus, i.e., to be used just one time. This would prevent patients from contracting some diseases due to contacting infected apparatus, and thus would be both practical and hygienic.

1 Claim, 5 Drawing Figures

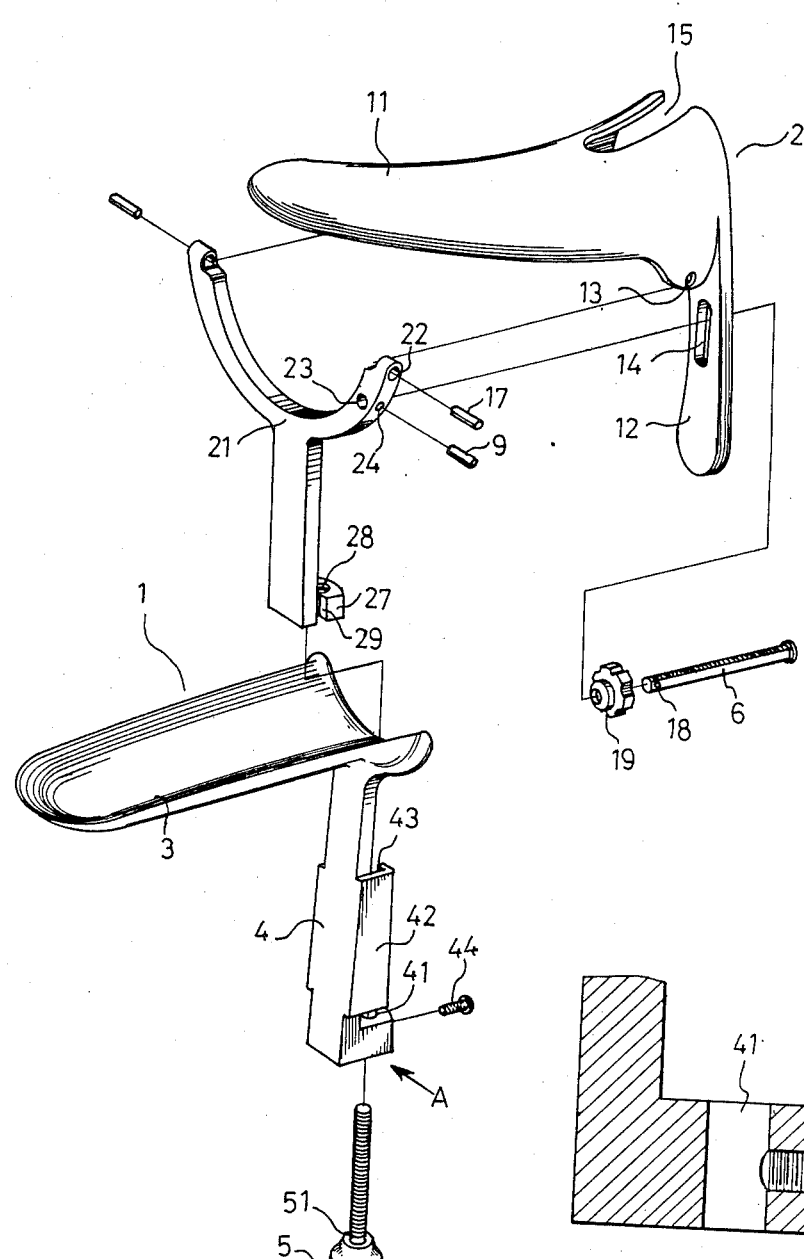

DISPOSABLE DUCKBILL SPECULUM

This application is a continuation-in-part application of Ser. No. 832,431, filed Feb. 24, 1986.

BACKGROUND OF THE INVENTION

This invention relates to a plastic or fiber-reinforced plastic duckbill speculum, and particularly relates to a gynecologic diagnostic apparatus. Further, because this duckbill speculum will be immediately disposed as soon as it has been used, the disposable apparatus according to the present invention can thereby ensure the diagnostic means are safe and hygienic.

In gynecology, the examination of the vagina is an important and frequent medical practice which deserves a great deal of attention. There are many cases where a woman is infected due to contact with an infected apparatus: Some of these disease are vulvitis, uterus infection, and ovaritis. Furthermore, some of these diseases make a woman sterile, or may even result in a stillbirth when the woman is pregnant.

In view of such a problem generally existing in gynecology, most of the hospitals and doctors use alcohol or the heat-sterilization method to sterilize those apparatus which will contact the patient's skin.

However, due to some species of germs with high resistance, or improper sterilization procedures, both two aforesaid sterilization methods cannot kill all germs on diagnostic apparatus. Therefore, a number of unfortnate female patients will be ineluctably infected with some serious diseases.

Due to the aforementioned drawbacks in using those conventional apparatus—they are too expensive to dispose after use end also may become disease mediums—the present application can be seen to be far superior.

A kind of gynecologic diagnostic apparatus which is made of relatively cheap materials so as to provide a disposable speculum to ensure a safe and hygienic diagnosis is hence eagerly desired.

SUMMARY

An purpose of the present invention is to provide a disposal gynecologic diagnostic speculum which is made of relatively cheap materials like plastics or fiber-reinforced plastics so as to ensure a safe and hygienic diagnosis.

Another purpose of the invention is to provide a gynecologic diagnostic speculum, which is constituted so that said duckbill speculum can safely be inserted and can easily stretch the vagina by rotating a bolt and subsequently open a space inside of the vagina and easily hold the angle open by rotating another bolt.

Further objectives and advantages of the invention will become more readily apparent from the ensuring specifications taken together with the drawings.

BRIEF DESCRIPTION OF THE DRAWINGS

FIG. 2 is an exploded view of FIG. 1;

FIG. 3 is a partially cross-sectional view from the arrow A in FIG. 2;

DETAILED DESCRIPTION OF THE PREFERRED EMBODIMENT

Figure 1:
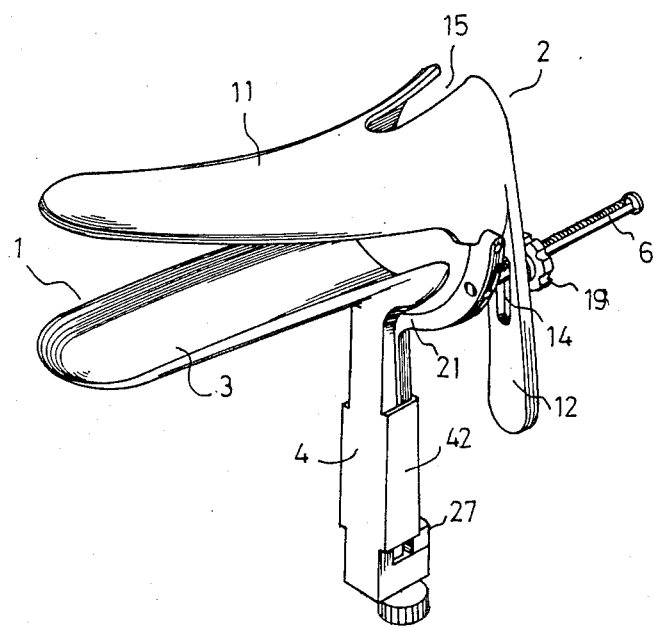
FIG. 1 is a perspective view showing a preferred embodiment of the present invention.

Firstly, referring to FIG. 2, it can be seen that the present invention consists of three main portions, of which one located left and lower is indicated as lower bill section 1, the other located right and upper is indicated upper bill section 2 and the third positioned between above-mentioned two sections 1 and 2 is indicated as support column 21. Further, there are also some connecting pieces used for connecting said three sections together, and for other specific purposes.

Referring to FIGS. 2 and 3, it can be seen that the upper part of the lower bill section 1 of the present invention, having a shape similar to the lower bill of a duck but with a rounder tip, is herein called lower bill 3. A L-shape stationary handle 4 has two parallel guide walls 42 set in its intermediate portion and two flanges 43 set on the edges of the guide walls 42 with two flanges extending towards each other. Further, a hole 41 which allows for a height adjustment bolt 5 to go through is vertically set in the lower protrudent portion of the stationary handle 4 (see FIG. 3). A horizontal threaded hole 45 is intersectingly set aside the vertical hole 41 as well as a screw 44 to secure height adjustment bolt 5 to the stationary handle 4. The lower bill section 1 of the present invention, including both lower bill 3 and stationary handle 4, is produced as one piece. The tip of the stationary handle 4 perpendicularly connects the lower bill 3 at the center of the rim of the bill 3.

As the same as the lower bill section 1, the upper bill section 2 consisting of both upper bill 11 and adjustable handle 12 is also produced as one piece. The side opposite from the bill tip of the upper bill 11 also has a semicircular rim which concaves towards the side opposite from said handle 12. A cut 15 set in the middle rim prevents the clitoris from being severely pressed. There are two connection holes 13 set at both ends of the rim.

The adjustable handle 12 with its tip connecting with the upper bill 11 at the right end of the rim (from the direction of the bill tip) has a shape like a spoon handle. A smooth-inside ellipstic adjustment hole 14 is also set in the intermediate area of adjustable handle 12 to allow for bolt 6 to go through and move within it.

The support column 21 has a semicircular rim on the upper portion and an L-shape column on the lower portion. There is a hole 22 set on each end of the semicircular rim. A bolt hole 23 set in the intermediate area of the right rim allows for the bolt 6 to go through. Further, a hole 24 which allows for a bolt fastener 9 to go through is set aside the bolt hole 23. A horizontal protrudent block 27 set on the lower end of the support column 21 has been set with a vertical threaded hole 28 thus allowing for the height adjustment bolt 5 to go through on its middle area. Both left and right sides on the face connecting with the vertical portion are set with a groove 29.

Figure 5:
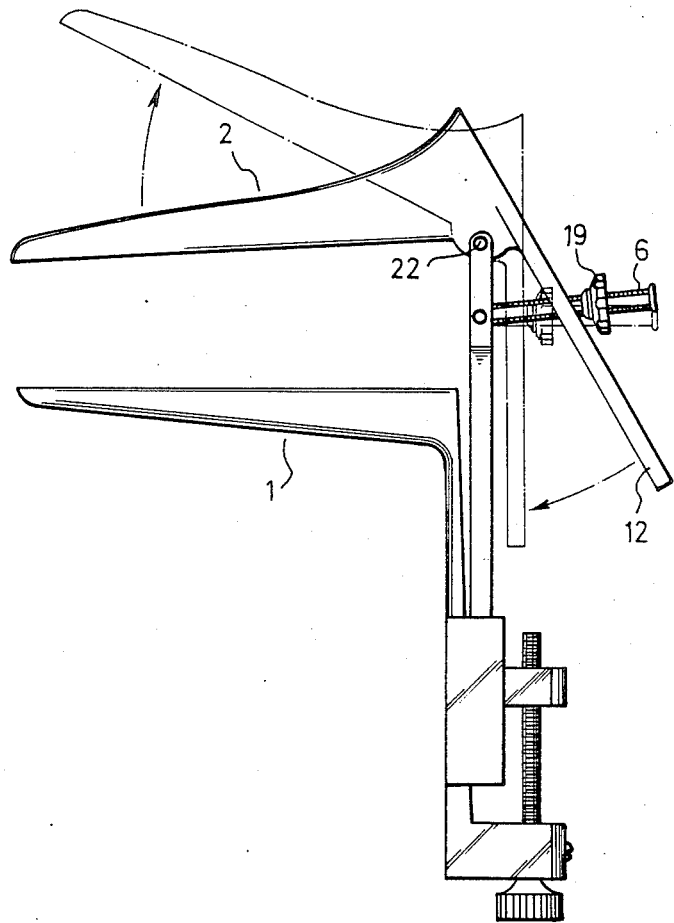
FIG. 5 is a schematic view respectively showing the subsequent opening operative statues after the procedures shown in FIG. 4.

Referring to FIGS. 2 and 5, it can be seen that the lower portion of the support column 21 may be inserted into the inner space which is surrounded by the guide walls 42 and flanges 43. The flanges 43 engage grooves 29 of the support column to enable the support column 21 to move up and down along the stationary handle 4 without disengagement. The upper bill section 2 and the support column 21 can be connected together by two bill fasteners 17 about which the upper bill section 2 can be rotated in both clockwise/counter-clockwise manners, thus allowing for the speculum to be opened to a desired angle when a force is applied on the adjustable handle 12 downwards. However, the opened bills will immediately close due to the dead weight of the upper bill 11 or additional outside inward pressure by the vagina when said force disappears.

Therefore, a bolt 6 and an adjustment nut 19 are adopted to solve the unwanted closures problem. Firstly, said bolt 6 is all threaded and secured on the rim portion of the support column 21 with a bolt fastener 9 going into the bolt-fixing hole 18 through a hole 23 on the side face of the rim of the support column 21. The other end of said bolt 6 goes through said adjustment hole 14 in said adjustable handle 12 and is subsequently screwed on said adjustment nut 19.

The height adjustment bolt 5, which has gone through the smooth holes 41 and the threaded hole 28 of which one is on the stationary handle 4 and the other is on the support column 21, is secured to said stationary handle 4 by way of a fixing screw 44 to go through a hole 45 and subsequently attaching the root 51 of threads of said bolt 5 (FIG. 3).

Figure 4:
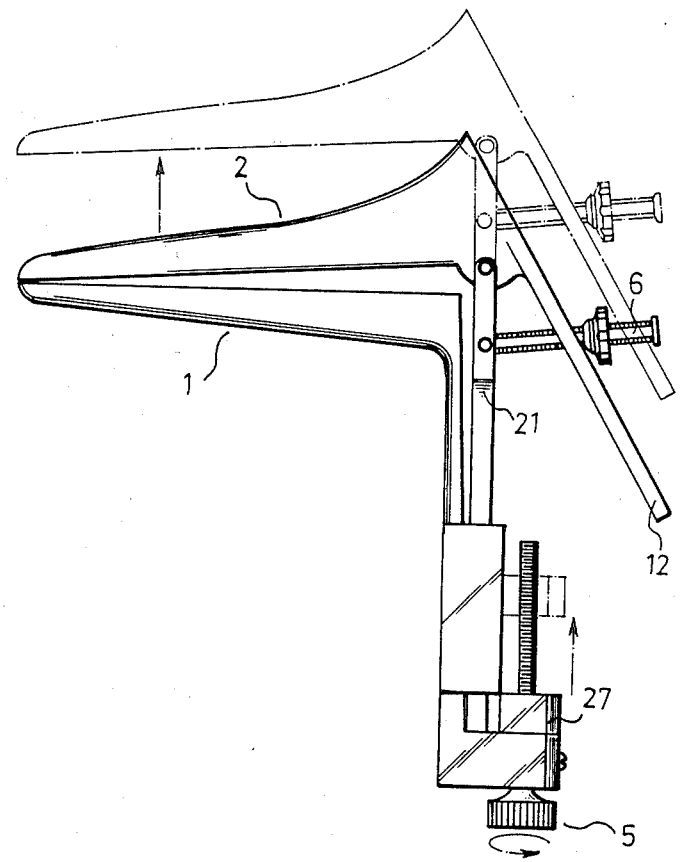
FIG. 4 is a schematic view respectively showing the widening operative statuses of the present invention.

By referring to the imaginary lines in FIG. 4, it can be seen that after the two bill portions 3 and 11 have been inserted into the vagina, the vagina may be opened to an appropriate width by rotating the height adjustment bolt 5 in a release direction.

Referring to FIG. 5, it can be seen that when the vagina is opened to a desired width by pressing the adjustable handle 12 inwards, said adjustment nut 19 on the bolt 6 can be adjusted towards and reach said adjustable handle 12 to keep the angle fixed and thus enable the doctor to begin the diagnosis.

According to the above descriptions, the disposable duckbill speculum can thereby be easily used and safely operated, thus providing a hygienic and practical apparatus for examining the vagina.

I claim:

1. A disposable gynecologic duckbill speculum made of plastics or fiber-reinforced plastics for examining the vagina comprising a lower bill section, an upper bill section, a support column and connecting pieces connecting said lower bill section, upper bill section and support column together, said lower bill section comprising a lower bill and a stationary handle in a manner of both said lower bill and said stationary handle being produced as one piece, said lower bill having a duckbill shape with a rounder tip and perpendicularly connecting the tip of said stationary handle with the center of the rim, said stationary handle looking like an L-shape column having two guide walls, together with two flanges on its tip, set on the intermediate area and having a hole set on the lower protrudent portion and also a hole set horizontally penetrating it through the circumference of said protrudent portion, said upper bill section comprising a duckbill-like upper bill with a round tip and an adjustable handle wherein said upper bill and said adjustable handle being produced as one piece, wherein said upper bill has two connection holes set around two ends on the rim, and the right rim of said upper bill connects the tip of said adjustable handle and thereby forms an appropriate angle, an elliptic adjustment hole being set on the intermediate area in said adjustable handle, aforementioned connecting pieces comprising a bolt being all threaded, an adjustment nut, two bill fasteners, one bolt fastener, a fixing screw and a height adjustment bolt, said fixing screw securing said height adjustment bolt to said lower bill section after said height adjustment bolt having connected said support column with said lower bill section, and said height adjustment bolt enabling said support column to be screwed up and be kept to a desired width, said bill fasteners securing said upper bill section to said support column, said bolt fastener securing the bolt to said support column, and said adjustment nut enabling said duckbill speculum to be adjusted and be kept to a desired opening angle.

* * * * *